(12) United States Patent
Soupart

(10) Patent No.: US 6,517,638 B1
(45) Date of Patent: Feb. 11, 2003

(54) METHOD OF AND DEVICE FOR CLEANING A SLIP RING

(75) Inventor: Ronald Jacques Joseph Soupart, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 24 days.

(21) Appl. No.: 09/744,728
(22) PCT Filed: Jun. 19, 2000
(86) PCT No.: PCT/EP00/05640
§ 371 (c)(1), (2), (4) Date: Jan. 29, 2001
(87) PCT Pub. No.: WO00/78216
PCT Pub. Date: Dec. 28, 2000

(30) Foreign Application Priority Data

Jun. 22, 1999 (EP) .............................. 99201994

(51) Int. Cl.[7] .................................. B08B 7/00
(52) U.S. Cl. .................. 134/6; 134/42; 15/97.1; 15/256.51
(58) Field of Search ............. 130/6, 7, 42; 15/97.1, 15/101, 256.51

(56) References Cited

U.S. PATENT DOCUMENTS

| | | | |
|---|---|---|---|
| 3,867,170 A | * 2/1975 | Ferguson et al. | 134/6 |
| 5,018,174 A | 5/1991 | Collins | 378/4 |
| 5,030,292 A | * 7/1991 | Koike et al. | 134/32 |
| 5,685,043 A | * 11/1997 | LaManna et al. | 15/256.5 |
| 6,253,413 B1 | * 7/2001 | Ohnuma et al. | 101/425 |
| 6,332,238 B1 | * 12/2001 | Hara et al. | 101/425 |

* cited by examiner

Primary Examiner—Randy Gulakowski
Assistant Examiner—Saeed Chaudhry
(74) Attorney, Agent, or Firm—John Vodopia

(57) ABSTRACT

The invention relates to a method of and a device for cleaning a slip ring which is rotatable about an axis of rotation, is supported by a frame and a circumferential surface of which is provided with a signal or power track which extends so as to be concentric with the axis of rotation. A chamois cloth drenched in a liquid is pressed against the circumferential surface provided with the track and the slip ring is rotated while the chamois cloth is kept pressed against the circumferential surface. The device includes a support which is to be connected to the frame supporting the slip ring and in relation to which the chamois cloth can be fixed. The support includes a pressure strip for pressing the chamois cloth against the circumferential surface of the slip ring provided with a track.

12 Claims, 1 Drawing Sheet

METHOD OF AND DEVICE FOR CLEANING A SLIP RING

The invention relates to a method of cleaning a slip ring which is arranged so as to be rotatable about an axis of rotation, is supported by a frame and a circumferential surface of which is provided with at least one signal or power track which extends concentrically about the axis of rotation.

Slip rings of this kind, customarily provided with a plurality of signal and/or power tracks, are used in a variety of devices, for example, in a tomography device controlled by a computer, for example, as disclosed in U.S. Pat. No. 5,018,174. Other devices, for example radar installations and the like, also utilize such slip rings.

During operation of devices provided with such slip rings it is from time to time necessary to clean the tracks in the slip rings in order to ensure continued correct transfer of signals and/or power. The customary method used to clean signal and/or audio tracks consists in the removal of the brush assemblies, co-operating with the tracks, from the supporting members for the brush assemblies which form part of the frame, and in providing said supporting members with supporting devices which support elongate rods. At the ends of said rods there are mounted cushions which are made of cotton or a similar material and serve to wipe the tracks clean.

The mounting of such a cleaning device is a very time-consuming operation and, moreover, it has been found in practice that the cleaning is often inadequate and that the cotton cushions leave particles and dirt behind in the tracks.

It is an object of the invention to provide a method of the kind set forth wherein the drawbacks of the method used thus far are mitigated.

This object can be achieved according to the invention in that a lining moistened with a liquid is pressed against the circumferential surface provided with the track, and in that the slip ring is rotated while keeping the lining pressed against the circumferential surface. Preferably, the lining may be formed by a chamois or synthetic material or cloth.

Surprisingly, it has been found that the tracks provided in slip rings can thus be effectively cleaned in a fast and simple manner, without it being necessary to remove parts, such as brush assemblies or the like, before commencing the cleaning of the slip ring. A track can be effectively cleaned by means of the chamois without the chamois itself giving off dirt.

Moreover, a plurality of adjacently situated tracks can be simultaneously cleaned by means of a chamois, so that particularly fast cleaning is achieved.

It has been found in practice that, whereas the cleaning of a slip ring by means of the described known method requires a period of time of approximately four hours, such cleaning can be performed by means of the method according to the invention within a period of time of approximately 20 minutes. The method according to the invention thus offers a substantial saving in respect of maintenance of the slip rings and, moreover, the device in which the slip ring is used need be put out of operation for a short period of time only so as to allow cleaning of the slip ring.

Alcohol is a preferred liquid for moistening or drenching the chamois.

Furthermore, use is preferably made of a lining made of a synthetic material, because such a synthetic lining has a constant thickness across its entire surface, as opposed to a natural chamois leather whose thickness is liable to vary across its surface.

Particularly thorough cleaning of a track can be realized by pressing the cloth by means of a member whose surface contacting the cloth has a shape which is essentially complementary to the circumferential surface of the slip ring wherein the track is provided. The cloth can then be suitably pressed against the boundary walls of the track.

According to a further aspect of the invention a particularly effective device for carrying out the method according to the invention is obtained by providing the device with a support which is to be connected to the frame supporting the slip ring and in relation to which the lining such as a chamois can be fixed, the support supporting a pressure strip for pressing the chamois against the circumferential surface of the slip ring provided with a track, said pressure strip being adjustable, relative to the support, between a first position, in which the pressure strip does not exert a pressure on the chamois, and a second position in which the pressure strip presses the chamois cloth against the circumferential surface of the slip ring.

The use of such a device enables the device to be quickly and simply connected to the frame supporting the slip ring, without it being necessary to remove brush assemblies or the like whereas, after the device has been installed and the chamois fitted between the pressure strip and the circumferential surface provided with a track, the chamois can be effectively pressed against the circumferential surface.

The chamois can be fitted in a location which is generally suitably accessible and visible, so that the device can be simply checked for correct operation.

The pressure strip is advantageously resiliently supported by the device, so that during operation the pressure strip is movable in a direction extending mainly perpendicularly to the circumferential surface of the slip ring. The pressure strip can thus follow irregularities, if any, in the circumferential surface of the slip ring during operation, thus maintaining suitable contact between the circumferential surface of the slip ring and the chamois.

The invention will be described in detail hereinafter with reference to an embodiment of a device according to the invention which is diagrammatically shown in the accompanying Figures.

Figure 1:
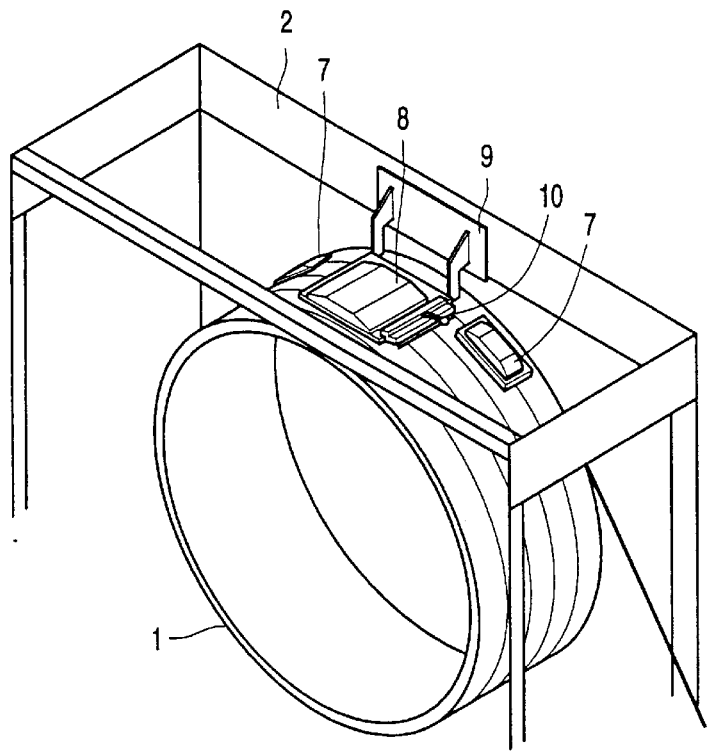
FIG. 1 shows diagrammatically a slip ring supported by a frame.

As is diagrammatically shown in FIG. 1, a part of a slip ring 1, forming part of a rotatable member which is not shown, is supported in a frame 2 by way of means which are not shown.

Figure 3:
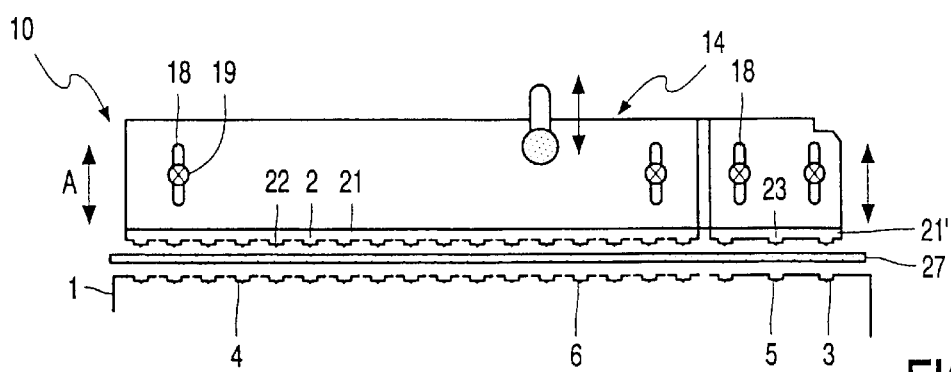
FIG. 3 is a view of the device shown in FIG. 1, taken in the direction of the arrow III in FIG. 2.

As is indicated in FIG. 3, a circumferential surface of such a slip ring 1 is provided with power tracks 3 and/or data tracks 4 which extend on the circumferential surface of the slip ring 1 so as to be concentric with the axis of rotation of the slip ring. As will be evident from FIG. 3, the tracks in the embodiment shown have a mainly rectangular or square cross-section; furthermore, a groove 5, 6 is recessed in the bottom of the tracks 3 and 4, respectively.

Power and data is transferred to/from these tracks via brush assemblies 7 for the transfer of power and brush assemblies 8 for the transfer of signals. Such brush assemblies are supported by supports which are mounted on the frame 2, for example like the support 9 which supports one of the brush assemblies 8.

Figure 2:
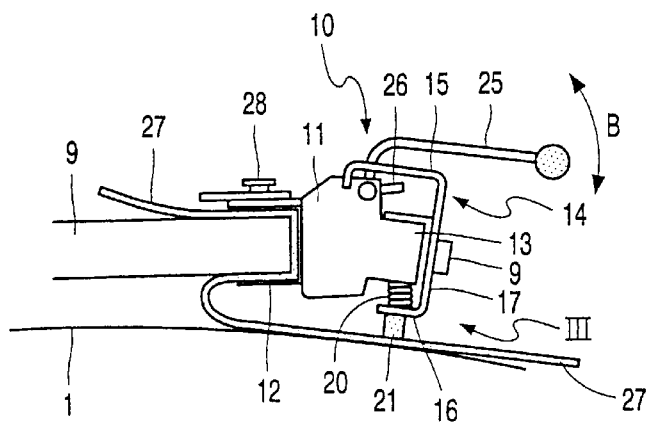
FIG. 2 is a diagrammatic side elevation of a device according to the invention.

The device 10 which is shown diagrammatically in the FIGS. 2 and 3 is used to lean the tracks.

Such a device is provided with an elongate support 11. A clamping strip 12, having a U-shaped cross-section, is attached to one side of the support 11. At the side facing the clamping strip 12 the support 11 is provided with a projecting nose 13 which extends along the support 11. Along the nose 13 there is provided a supporting strip 14 which has a mainly U-shaped cross-section and is provided with two legs 15 and 16, extending parallel to one another, and a member 17 which interconnects the ends of said legs. The member 17 is provided with slotted holes 18 (FIG. 3) which extend perpendicularly to the longitudinal direction of said member. The threaded shafts of bolts 19 are inserted through said slotted holes 18. The threaded shafts of the bolts 19 are screwed into threaded holes in the projecting nose 13 of the support 11, the arrangement being such that the member 17 of the supporting strip 14 is located between the projecting nose 13 and the heads of the bolts 19. The construction is such that the member can be slid to and fro in a direction parallel to the longitudinal direction of the slotted holes 18; this is indicated by means of the arrow A in FIG. 3.

Between the lower leg 16 of the supporting strip 14 and the lower side of the projecting nose there are provided compression springs 20 which tend to push the supporting strip 14 downwards, viewed in the FIGS. 2 and 3.

Two pressure strips 21 and 21' are attached to the lower side of the pressure strip 14 in the embodiment shown. As is shown in FIG. 3, the pressure strip 21 is provided with projecting parts 22 which are situated so as to face the signal tracks 4 and whose shape is adapted to the shape of the signal grooves 20. Analogously, the pressure strip 21' is provided with projecting parts 23 whose shape matches the shape of the power tracks 3.

Furthermore, the support 11 supports a shaft 24 which extends in the longitudinal direction of the support and is pivotable to and fro, by way of a lever 25 secured to the shaft, as indicated by means of the arrow B in FIG. 2.

Also connected to the shaft is an arm 26 which extends underneath the leg 15 of the supporting strip 14.

As is shown in the FIGS. 1 and 2, the described device 10 can be connected to the support 9 of the brush assemblies 8 by sliding the clamping strip 12, having a U-shaped cross-section, over an edge of the support 9. Before the clamping strip 12 is slid over the edge of the support 9, the end of a chamois cloth 27 is arranged in the clamping strip 12 in such a manner that this end of the chamois cloth is clamped onto the support 9 by the clamping strip 12 when clamping screws 28 provided in the clamping strip 12 are tightened.

As is particularly clearly shown in FIG. 2, the chamois, drenched in alcohol prior to fitting, is fitted so that the chamois 27 extends between the circumferential plane of the slip ring 1, provided with tracks 3, 4, and the parts 22 and 24 of the pressure strips 21 and 21' facing the slip ring. Furthermore, the construction is such that the width of a projecting part 22 plus by twice the thickness of the chamois 27 corresponds approximately to the width of a signal track 4. Similarly, the width of a projecting part 23 of the pressure strip 21' plus twice the thickness of the chamois 27 corresponds approximately to the width of a power track 3. Furthermore, the ends of the projecting parts 20 and 21 which face the slip ring are provided with projecting shoulders which correspond to the grooves 5, 6 recessed in the tracks.

In the position shown in FIG. 2 the arm 26 is clear of the lower side of the leg 15 of the supporting strip 14, so that the springs 20 can freely press the supporting strip downwards and the chamois is pressed against the circumferential surface of the slip ring and into the tracks 4, 5 by the pressure strips 21, 21" in order to realize effective cleaning of the tracks. After the cleaning of the tracks, the lever 25 will be pivoted counter-clockwise (viewed in FIG. 2), so that the end of the arm 26 which is connected to the shaft 24 contacts the lower side of the leg 15 of the supporting strip 14. When the shaft 24 is pivoted further by means of the lever 25, the supporting strip will be pressed upwards by the arm 26, so that the pressure strips 21, 21' come clear of the chamois cloth 27 and the slip ring 21. The construction is such that during the counter-clockwise pivoting of the arm 26 (viewed in FIG. 2) in order to move the pressure strips 21, 21' clear of the circumferential surface of the slip ring 1, the arm 26 passes a position in which it extends perpendicularly to the lower surface of the leg 15 which co-operates with the arm 26, so that the supporting strip cannot be moved back from this disengaged position under the influence of the spring force exerted by the springs 20. Subsequently, the device 10 can be removed again and the device in which the slip ring is accommodated can be put into operation again.

What is claimed is:

1. A method of cleaning a slip ring which is arranged so as to be rotatable about an axis of rotation, is supported by a frame and a circumferential surface of which is provided with at least one signal or power track which extends concentrically about the axis of rotation, comprising a lining moistened with a liquid and pressed against the circumferential surface provided with the track, and that the slip ring is rotated while keeping the lining pressed against the circumferential surface.

2. A method as claimed in claim 1, wherein a plurality of adjacently situated tracks are simultaneously cleaned by means of the lining.

3. A method as claimed in claim 1, wherein the lining is drenched in alcohol.

4. A method as claimed in claim 1, wherein the lining is made of a synthetic material.

5. A method as claimed in claim 1, wherein the lining is pressed by means of a member whose surface contacting the lining has a shape which is mainly complementary to the shape of the circumferential surface of the slip ring provided with the track.

6. A method as claimed in claim 1, wherein the method is used to clean the signal and power tracks of a computer-controlled tomography device.

7. A device for cleaning a slip ring, comprising a support attached to a frame supporting the slip ring and in relation to which a lining can be fixed, the support supporting a pressure strip for pressing the lining against the circumferential surface of the slip ring provided with a track, said pressure strip being adjustable, relative to the support, between a first position, in which the pressure strip does not exert pressure on the lining, and a second position, in which the pressure strip presses the lining against the circumferential surface of the slip ring.

8. A device as claimed in claim 7, wherein the pressure strip is resiliently supported by the device so that the pressure strip is movable in a direction extending mainly perpendicularly to the circumferential surface of the slip ring.

9. A device as claimed in claim 7, wherein the device is provided with fixing means whereby the device can be attached to a support for brushes co-operating with the slip ring.

10. A device as claimed in claim 7, wherein the pressure strip is attached to a supporting member which is subject to springs which are arranged between the supporting member and the support.

11. A device as claimed in claim 10, wherein the supporting member is provided with slotted holes which extend mainly perpendicularly to the longitudinal direction of the supporting member and wherethrough bolts for coupling the supporting member to the support are passed in such a manner that the supporting strip is slidable, relative to the support, in the longitudinal direction of the slotted holes.

12. A device as claimed in claim 7, wherein the device is constructed so as to be used for cleaning the signal and power tracks of a computer-controlled tomography device.

* * * * *